United States Patent [19]
Green

[11] 3,992,422
[45] Nov. 16, 1976

[54] PROCESS FOR THE PREPARATION OF 21-HALOGENO-21-DESOXY-17α-ACYLOXY-20-KETO-PREGNENES

[75] Inventor: Michael J. Green, Kendall Park, N.J.

[73] Assignee: Schering Corporation, Kenilworth, N.J.

[22] Filed: Aug. 14, 1975

[21] Appl. No.: 604,672

[52] U.S. Cl.................... 260/397.45; 260/239.55 D
[51] Int. Cl.² ............................................ C07J 5/00
[58] Field of Search.... 260/397.45, 397.4, 239.55 D

[56] References Cited
UNITED STATES PATENTS 3,743,636   7/1973   Hartmann et al. ......... 260/239.55 R
3,755,302   8/1973   Ercoli et al. ............... 260/239.55 R
3,832,366   8/1974   Cimarusti................... 260/239.55 D Primary Examiner—Elbert L. Roberts
Attorney, Agent, or Firm—Mary S. King

[57] ABSTRACT

21-Halogeno-17α-acyloxy-20-keto-4-pregnenes having physiological properties are prepared by the reaction of a 17α,21-dihydroxy-20-keto-4-pregnene 17α,21-orthoester with a halide reagent selected from the group consisting of triarylsilyl halides and tri-lower alkylsilyl halides in an organic solvent, said halide being chloride or bromide. Preferred reagents are tri-lower alkylsilyl halides, particularly trimethylsilyl chloride.

7 Claims, No Drawings

PROCESS FOR THE PREPARATION OF 21-HALOGENO-21-DESOXY-17α-ACYLOXY-20-KETO-PREGNENES

FIELD OF INVENTION

This invention relates to a novel process for the manufacture of 21-halogeno-17α-acyloxy-20-ketopregnenes.

More specifically, this invention relates to a process for preparing 21-chloro- and 21-bromo-17α-hydrocarboncarbonyloxy-20-keto-4-pregnenes which are known, physiologically active steroids.

PRIOR ART

Known in the art are 21-chloro- and 21-bromo-17α-acyloxy-20-keto-4-pregnenes and the 1-dehydro-, 6-dehydro- and 1,6-bis-dehydro analogs thereof which possess progestational, glucocorticoid and anti-inflammatory activities.

The prior art methods for preparing the 21-chloro- and 21-bromo-17α-acyloxy-20-keto-4-pregnenes involve multistep sequences of reactions. One method comprises converting the 17α,21-dihydroxy pregnene to the 21-sulfonate ester thereof followed by reaction with an inorganic chloride or bromide to yield the corresponding 21-chloro- or 21-bromo-17α-hydroxy-4-pregnene, and thence selective acylation of the 17α-hydroxyl group (during which step acylation of the 11β-hydroxyl group or aromatization of the A-ring may occur unless the 11β-hydroxyl and/or the 3-keto functions are protected, which requires additional steps) to give the 21-chloro- or 21-bromo-17α-acyloxy-4-pregnene. In another such method, a 17α,21-dihydroxy pregnene is converted to the corresponding 17α,21-cyclic orthoester, then selectively hydrolyzed to the 17α-ester, after which the 21-hydroxyl group is converted to the 21-chloro group via the 21-sulfonate, a step which requires forcing conditions (e.g. high temperatures) and which proceeds at a slow rate. Each of the foregoing routes involves a selective reaction which can be difficult and which involves three or four steps.

By the process of this invention, good yields of pure 21-halogeno-17α-acyloxy-20-ketopregnenes are easily prepared in one step from the 17α,21-orthoester by reaction with a triarylsilyl halide or a trialkylsilyl halide without the necessity of protecting other functional groups (e.g. the 3-ketone or 11β-hydroxyl) present in the molecule and thence removing the protecting groups when the process is completed.

In my copending application Ser. No. 604,673 filed Aug. 14, 1975, is also described and claimed the process for preparing 21-halogeno-17α-acyloxy-20-ketopregnenes from a 17α,21-orthoester utilizing triphenylmethyl chloride or bromide as reagent. The process of the instant invention advantageously produces higher yields of pure product which, when lower alkylsilyl halides are used as reagents, do not require purification by time-consuming chromatographic techniques which, when triphenylmethyl halide reagents are used, are necessary to separate the 21-halogeno-17α-acyloxy-20-ketopregnene products from the coproduced tritylalkyl ethers and/or excess halide reagent. In addition to the foregoing, tri-lower alkylsilyl halide reagents are less costly and easier to handle in the claimed process then the triphenylmethyl halide reagents.

GENERAL DESCRIPTION OF THE INVENTION

The process of this invention, whereby a 17α,21-dihydroxy-20-ketopregnene 17α,21-orthoester is converted to a 21-halogeno-17α-acyloxy-20-ketopregnene, is defined as the process for the preparation of a 21-halogeno-17α-acyloxy-20-ketopregnene, said halogeno being chloro or bromo, which comprises reacting a 17α,21-dihydroxy-20-ketopregnene 17α,21-orthoester with a halide reagent selected from the group consisting of triarylsilyl halide and tri-lower alkylsilyl halide, said halide being chloride or bromide, in an organic solvent.

Of the 21-halogeno-17α-acyloxy-20-ketopregnenes prepared by the process of this invention, those specifically contemplated include 4-pregnenes of the following formula I and the 1-dehydro-, 6-dehydro- and 1,6-bis-dehydro analogs thereof:

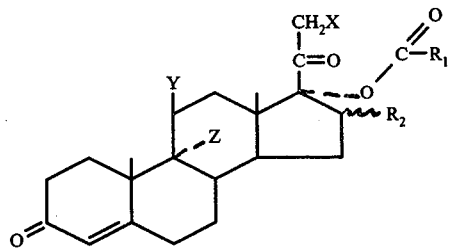

wherein
X is chlorine or bromine;
Y is hydrogen, oxo, hydroxy, lower alkanoyloxy, chlorine or fluorine;
Z is hydrogen, fluorine, chlorine or bromine when Y is oxo, hydroxy or lower alkanoyloxy; Z is chlorine or bromine when Y is chlorine or fluorine and Z is hydrogen when Y is hydrogen
$R_1$ is alkyl of 1 to 8 carbon atoms, or phenyl; and
$R_2$ is hydrogen, α-methyl, β-methyl, α-acyloxy of the formula

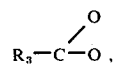

wherein $R_3$ is a lower alkyl having 1 to 8 carbon atoms.

The foregoing are known compounds possessing, in general, progestational, glucocorticoid and anti-inflammatory activities and, as such, can be used in the same manner as other known progestational and anti-inflammatory agents. The foregoing are particularly useful as topical anti-inflammatory agents, a preferred group of compounds prepared by my process being the 1-dehydro analogs of formula I, particularly those wherein X is chlorine, said compounds having high topical activity.

The halide reagents used in this process are known compounds which are either commercially available or are easily prepared via known procedures.

Typical reagents include tri-lower alkylsilyl halides such as trimethylsilyl chloride, triethylsilyl chloride, tri-(n-propyl)silyl chloride, tri-(n-butyl)silyl chloride, tri-(n-pentyl)silyl chloride, tri-(n-hexyl)silyl chloride and the corresponding tri-lower alkyl bromides as well as tri-arylsilyl halides such as triphenylsilyl chloride and methyl substituted derivatives thereof such as tri-(p-tolyl)silyl chloride, tri-(m-tolyl)silyl chloride, and the corresponding tri-arylsilyl bromides. Preferred reagents in this process are the tri-lower alkylsilyl halides, particularly trimethylsilyl chloride and trimethylsilyl bromide. Both the triphenylmethyl halide reagents used in the process of my copending application Ser. No. 604,673 filed Aug. 14, 1975, and the triphenylsilyl halide reagents are solids, so that rigorous chromatographic techniques are required to remove the co-produced triphenylmethyl alkyl ethers or triphenylsilyl alkyl ethers as well as any excess reagent from the 21-halogeno-17α-acyloxy-20-keto-4-pregnene products produced by reaction thereof with a 17α,21-dihydroxy-20-ketopregnene 17α,21-orthoester. In contrast, trimethylsilyl bromide and trimethylsilyl chloride are low boiling liquids, are readily soluble in organic solvents and are easily removed by distillation after completion of the reaction together with the co-produced, low boiling, trialkylsilyl alkyl ethers, thus resulting in higher yields of purer products which do not necessarily require chromatographic techniques to obtain pure samples of the 21-halogeno-17α-acyloxy-20-keto-4-pregnene products. In addition to the foregoing, the trialkylsilyl bromide and chloride reagents are advantageously less expensive than triphenylmethyl halides or triphenylsilyl halides and produce excellent yields of the 21-halogeno-17α-acyloxy-20-keto-4-pregnene.

That reaction of a 17α,21-orthoester of a 17α,21-dihydroxy-20-ketopregnene with a triarylsilyl chloride or bromide or with a tri-lower alkylsilyl chloride or bromide will produce a 21-chloro- or 21-bromo-17α-acyloxy-20-ketopregnene in good yields, is surprising since I have discovered that the corresponding fluoride reagents will not produce a 21-fluoro-17α-acyloxy-20-ketopregnene. Moreover, I have found that reaction of a 17α,21-dihydroxy-20-ketopregnene 17α,21-orthoester (e.g. prednisolone 17,21-ethylorthopropionate) with tert.-butyl chloride (which is the carbon analog of trimethylsilyl chloride) in methylene chloride does not produce a 21-chloro-17α-acyloxy-20-ketopregnene. Additionally, when trimethylgermanium chloride and tri-n-butylstannyl chloride are substituted as reagents in my process, a 21-halogeno-17α-acyloxy-20-ketopregnene is not produced even though the foregoing reagents are corresponding derivatives of metals of the same group (i.e. IVa) of the Periodic Table as silicon.

My process is preferably carried out in an organic solvent in which both the steroid starting compound and the reagents are soluble and which will not react with the reagent so that competing side reactions are minimized. Suitable organic solvents for this process include 1,2-dimethoxyethane (glyme); bis(2-methoxyethyl)ether (diglyme); cyclic ethers such as dioxane and tetrahydrofuran; and preferably halogenated hydrocarbons such as carbon tetrachloride, chloroform, ethylene dichloride and, in particular, methylene chloride.

My process is usually carried out at the reflux temperature of the solvent, preferably methylene chloride, until the reaction is completed as determined by thin layer chromatography (usually from 2 to 22 hours). The reaction is advantageously run under anhydrous conditions and may be carried out under an inert atmosphere, e.g. under argon or nitrogen; however, this is not necessary.

The requisite starting compounds of my process are 17α,21-orthoesters of the 17α,21-dihydroxy analogs of the compounds defined by formula I. The orthoesters are obtained from the corresponding 17α,21-dihydroxy-20-ketopregnenes by known reaction with a trialkyl orthoester in a polar organic solvent, e.g. dimethylformamide or dimethylsulfoxide, in the presence of an acid catalyst, e.g. p-toluenesulfonic acid. The reaction may be carried out under an inert atmosphere, e.g. nitrogen or argon, but this is not necessary. The reaction is usually carried out at room temperature for a period of time ranging from 2 to 24 hours; however, when preparing a 17α,21-alkylorthobenzoate, the reaction is preferably carried out in dioxane/benzene at reflux temperature.

Specifically, the starting compounds of my process include 17α,21-dihydroxy-20-ketopregnene 17α,21-orthoesters having the following formula II:

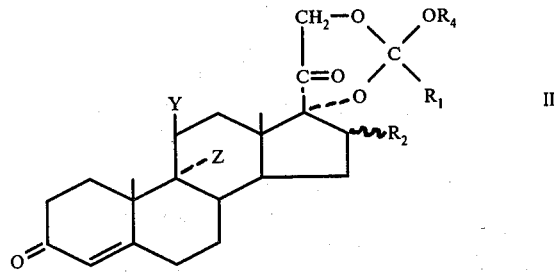

wherein
Y is hydrogen, oxo, hydroxy, lower alkanoyloxy, chlorine or fluorine;
Z is hydrogen, fluorine, chlorine or bromine when Y is oxo, hydroxy or lower alkanoyloxy; Z is chlorine or bromine when Y is chlorine or fluorine; and Z is hydrogen when Y is hydrogen;
$R_1$ is alkyl of 1 to 8 carbon atoms, or phenyl;
$R_2$ is hydrogen, α-methyl, β-methyl, α-acyloxy of the formula

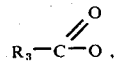

wherein $R_3$ is a lower alkyl having 1 to 8 carbon atoms;
$R_4$ is alkyl having 1 to 4 carbon atoms; and
the 1-dehydro-, 6-dehydro- and 1,6-bis-dehydro analogs thereof.

Compounds of formula II are made by reaction of the corresponding 17α,21-dihydroxy steroid with trialkyl orthoester of the formula

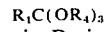

wherein $R_1$ is alkyl of 1 to 8 carbon atoms or phenyl; and $R_4$ is an alkyl of 1 to 4 carbon atoms.

In a preferred mode of carrying out my process, to one mole of a steroidal 17α,21-orthoester of formula II in a halogenated solvent (usually methylene chloride) there is added at least an equimolar amount (and usually about 5 moles per mole of steroid) of a halide reagent selected from the group consisting of tritolylsilyl halide, triphenylsilyl halide and tri-lower alkylsilyl halide, said halide being chloride or bromide, preferred reagents being trimethylsilyl chloride or trimethylsilyl bromide. The reaction is heated at reflux temperature (optionally under an inert atmosphere) until the reaction is completed as determined by thin layer chromatography (usually 2 to 24 hours). The resulting 21-halogeno-17α-acyloxy-20-keto-4-pregnene is then isolated utilizing conventional techniques, such as via chromatographic techniques or by crystallization, usually in yields of from 30% to 65% when the starting steroid is a 1,4-pregnadiene.

When carrying out my reaction with trimethylsilyl bromide with steroids possessing an 11-hydroxyl function, an 11-trimethylsilyl ether sometimes forms, which is easily converted to the 11-hydroxyl derivative via acid hydrolysis.

The following examples illustrate specific embodiments of the invention, but are not to be considered as limiting the scope of the invention, obvious equivalents of which, apparent to one skilled in the art, being considered as included within the scope of this invention.

PREPARATION OF INTERMEDIATES

PREPARATION 1

9α,11β-dichloro-16α-methyl-1,4-pregnadiene-17α,21-diol-3,20-dione 17,21-methylorthobenzoate and the 1,2-dihydro analog thereof A. To a solution of 2 gms. of 9α,11β-dichloro-16α-methyl-1,4-pregnadiene-17α,21-diol-3,20-dione in 112 ml. of dioxane and 168 ml. of benzene add 2 ml. of trimethylorthobenzoate and 200 mg. of pyridinium p-toluenesulfonate and heat at reflux temperature for 24 hours. Add an additional 2 ml. portion of trimethylorthobenzoate and 200 mg. of pyridinium p-toluenesulfonate and heat at reflux temperature for 3 more days. Distill off about two-thirds of the solvent, add about 6 drops of pyridine and then distill the remaining solvent in vacuo at room temperature. Triturate the resulting residue with petroleum ether and decant the petroleum ether wash to obtain a residue comprising 9α,11β-dichloro-16α-methyl-1,4-pregnadiene-17α,21-diol-3,20-dione 17,21-methylorthobenzoate, which is used without further purification in the process of this application.

B. In a manner similar to that described in above Preparation 1A, treat 9α,11β-dichloro-16α-methyl-4-pregnene-17α,21-diol-3,20-dione in dioxane and benzene with trimethylorthobenzoate and pyridinium p-toluenesulfonate; evaporate the solvents, then wash the resultant product with petroleum ether in a manner similar to that described to obtain 9α,11β-dichloro-16α-methyl-4-pregnene-17,21-diol-3,20-dione 17,21-methylorthobenzoate.

PREPARATION 2

1,4-Pregnadiene-11β,17α,21-Triol-3,20-Dione 17,21-n-Butylorthopropionate and the 1,2-Dihydro Analog Thereof A. To a solution of 2 gms. of 1,4-pregnadiene-11β,17α,21-triol-3,20-dione in 10 ml. of dimethylsulfoxide add 150 mg. of p-toluenesulfonic acid and 3.6 ml. of tri-n-butylorthopropionate. Stir the reaction mixture at room temperature for 3.5 hours, then pour onto 600 ml. of ice water to which has been added 300 ml. of saturated sodium bicarbonate solution. Separate the resultant precipitate by filtration and wash the precipitate with copious amounts of water. Dissolve the precipitate in ethyl acetate. Dry the ethyl acetate solution over anhydrous magnesium sulfate and evaporate in vacuo to a residue comprising 1,4-pregnadiene-11β,17α,21-triol-3,20-dione 17,21-n-butylorthopropionate.

B. In similar manner, treat 4-pregnene-11β,17α,21-triol-3,20-dione in dimethylsulfoxide with p-toluenesulfonic acid and tri-n-butylorthopropionate to obtain 4-pregnene-11β,17α,21-triol-3,20-dione 17,21-n-butylorthopropionate.

PREPARATION 3

9α,11β-Dichloro-16α-Methyl-1,4-Pregnadiene-17α,21-Diol-3,20-Dione 17,21-n-butylorthopropionate and the 1,2-Dihydro Analog Thereof A. To a solution of 2 gm. of 9α,11β-dichloro-16α-methyl-1,4-pregnadiene-17α,21-diol-3,20-dione in 12 ml. of dimethylsulfoxide add 150 mg. of p-toluenesulfonic acid and 3.6 ml. of tri-n-butylorthopropionate. Stir the reaction mixture at room temperature for 4 hours, then pour onto 600 ml. of ice water, to which has been added 300 ml. of saturated sodium bicarbonate solution. Separate the resultant precipitate by filtration and wash the precipitate with copious amounts of water. Dissolve the precipitate in ethyl acetate, dry the ethyl acetate over anhydrous magnesium sulfate and evaporate in vacuo to a residue comprising 9α,11β-dichloro-16α-methyl-1,4-pregnadiene-17α,21-diol-3,20-dione 17,21-n-butylorthopropionate.

B. In similar manner, treat 9α,11β-dichloro-16α-methyl-4-pregnene-17α,21-diol-3,20-dione in dimethylsulfoxide with p-toluenesulfonic acid and tri-n-butylorthopropionate to obtain 9α,11β-dichloro-4-pregnene-17α,21-diol-3,20-dione 17,21-n-butylorthopropionate.

PREPARATION 4

9α,11β-dichloro-16α-methyl-1,4-pregnadiene-17α,21-diol-3,20-dione 17,21-n-butylorthovalerate and the 1,2-dihydro analog thereof A. To a solution of 2 gm. of 9α,11β-dichloro-16α-methyl-1,4-pregnadiene-17α,21-diol-3,20-dione in 12 ml. of dimethylsulfoxide add 150 mg. of p-toluenesulfonic acid and 4 ml. of tri-n-butylorthovalerate. Stir at room temperature for 4 hours, then add 600 ml. of ice water, to which has been added 300 ml. of saturated sodium bicarbonate. Isolate the resultant product in a manner similar to that described in Preparation 3A to obtain 9α,11β-dichloro-16α-methyl-1,4-pregnadiene-17α,21-diol-3,20-dione 17,21-n-butylorthovalerate.

B. Treat a solution of 9α,11β-dichloro-16α-methyl-4-pregnene-17α,21-diol-3,20-dione in dimethylsulfoxide with p-toluenesulfonic acid and tri-n-butylorthovalerate in a manner similar to that described hereinabove to obtain 9α,11β-dichloro-16α-methyl-4-pregnene-17α,21-diol-3,20-dione-3,20-dione 17,21-n-butylorthovalerate.

PREPARATION 5

9α-fluoro-16β-methyl-1,4-pregnadiene-11β,17α,21-triol-3,20-dione 17,21-n-butylorthopropionate and the 1,2-dihydro analog thereof A. In a manner similar to that described in Preparation 2A, treat 3 gm. of 9α-fluoro-16β-methyl-1,4-pregnadiene-11β,17α,21-triol-3,20-dione in 9 ml. of dimethylsulfoxide with 225 mg. of p-toluenesulfonic acid and 5.4 ml. of tri-n-butylorthopropionate at room temperature for 4 hours. Isolate and purify the resultant product in a manner similar to that described to obtain 9α-fluoro-16β-methyl-1,4-pregnadiene-11β,17α,21-triol-3,20-dione 17,21-n-butylorthopropionate.

B. In a manner similar to that described hereinabove, treat 9α-fluoro-16β-methyl-4-pregnene-11β,17α,21-triol-3,20-dione in dimethylsulfoxide with p-toluenesulfonic acid and tri-n-butylorthopropionate to obtain 9α-fluoro-16β-methyl-4-pregnene-11β,17α,21-triol-3,20-dione 17,21-n-butylorthopropionate.

PREPARATION 6

16α-methyl-1,4-pregnadiene-11β,17α,21-triol-3,20-dione 17,21-n-butylorthopropionate and the 1,2-dihydro analog thereof A. To a solution of 0.75 gm. of 16α-methyl-1,4-pregnadiene-11β,17α,21-triol-3,20-dione in 3.75 ml. of dimethylsulfoxide add 56.5 mg. of p-toluenesulfonic monohydrate and 2.25 ml. of tri-n-butylorthopropionate and stir the reaction mixture at room temperature for 3 hours. Pour into a mixture of 400 ml. of ice water and 100 ml. of saturated sodium bicarbonate solution. Decant the aqueous layer and triturate the gummy residue with hexane. Separate the resultant precipitate by filtration and dry at room temperature in vacuo to obtain 16α-methyl-1,4-pregnadiene-11β,17α,21-triol-3,20-dione 17,21-n-butylorthopropionate (yield 0.87 gm.).

B. In a manner similar to that described hereinabove, treat 16α-methyl-4-pregnene-11β,17α,21-triol-3,20-dione in dimethylsulfoxide with p-toluenesulfonic monohydrate in tri-n-butylorthopropionate and isolate the resultant product in the described manner to obtain 16α-methyl-4 -pregnene-11β,17α,21-triol-3,20-dione 17,21-n-butylorthopropionate.

PREPARATION 7

9α-fluoro-16α-methyl-1,4-pregnadiene-11β,17α,21-triol-3,20-dione 17,21-methylorthobenzoate and the 1,2-dihydro analog thereof A. To 1 gm. of 9α-fluoro-16α-methyl-1,4-pregnadiene-11β,17α,21-triol-3,20-dione in 64 ml. of dioxane and 84 ml. of benzene add 1 ml. of trimethylorthobenzoate and 100 mg. of pyridinium p-toluenesulfonate. Heat the reaction mixture at reflux temperature for 3 days, then distill two-thirds of the solvent at atmospheric pressure, add 5 drops of pyridine, then distill the remaining solvent in vacuo at room temperature. Triturate the resultant residue with petroleum ether and filter the resultant solid comprising 9α-fluoro-16α-methyl-1,4-pregnadiene-11β,17α,21-triol-3,20-dione 17,21-methylorthobenzoate.

B. Treat 9α-fluoro-16α-methyl-4-pregnene-11β,17α,21-triol-3,20-dione in dioxane and benzene with trimethylorthobenzoate and pyridinium p-toluenesulfonate in the manner described hereinabove to obtain 9α-fluoro-16α-methyl-4-pregnene-11β,17α,21-triol-3,20-dione 17,21-methylorthobenzoate.

PREPARATION 8

9α-fluoro-16α-methyl-1,4-pregnadiene-11β,17α,21-triol-3,20-dione 17,21-n-butylorthopropionate and the 1,2-dihydro analog thereof A. In a manner similar to that described in Preparation 6A, treat 9α-fluoro-16α-methyl-1,4-pregnadiene-11β,17α,21-triol-3,20-dione in dimethylsulfoxide with p-toluenesulfonic monohydrate and tri-n-butylorthopropionate. Isolate and purify the 9α-fluoro-16α-methyl-1,4-pregnadiene-11β,17α,21-triol-3,20-dione 17,21-n-butylorthopropionate.

B. In a manner similar to that described hereinabove, treat 9α-fluoro-16α-methyl-4-pregnene-11β,17α,21-triol-3,20-dione in dimethylsulfoxide with p-toluenesulfonic monohydrate and tri-n-butylorthopropionate to obtain 9α-fluoro-16α-methyl-4-pregnene-11β,17α,21-triol-3,20-dione 17,21-n-butylorthopropionate.

PREPARATION 9

1,4,6-pregnatriene-11β,17α,21-triol-3,20-dione 17,21-n-butylorthopropionate and the 1,2-dihydro analog thereof A. To a solution of 60 mg. of 1,4,6-pregnatriene-11β,17α,21-triol-3,20-dione in 0.5 ml. of dimethylsulfoxide add 5 mg. of p-toluenesulfonic acid and 0.3 ml. of tri-n-butylorthopropionate. Stir at room temperature for 3 hours, pour into saturated sodium bicarbonate solution and extract with ethyl acetate. Dry the combined ethyl acetate extracts over magnesium sulfate, then evaporate in vacuo to a residue comprising 1,4,6-pregnatriene-11β,17α,21-triol-3,20-dione 17,21-n-butylorthopropionate.

B. In a manner similar to that described hereinabove, treat 4,6-pregnadiene-11β,17α,21-triol-3,20-dione in dimetylsulfoxide with p-toluenesulfonic acid and tri-n-butylorthopropionate to obtain 4,6-pregnadiene-11β,17α,21-triol-3,20-dione 17,21-n-butylorthopropionate.

PREPARATION 10

9α-Fluoro-16β-Methyl-17α,21-Diol-3,11,20-Trione 17,21-methylortho-n-butyrate and the 1,2-Dihydro Analog Thereof A. In a manner similar to that described in Preparation 4A, treat 9α-fluoro-16β-methyl-1,4-pregnadiene-11β,17α-diol-3,11,20-trione in dimethylsulfoxide with p-toluenesulfonic acid and trimethylortho-n-butyrate. Isolate and purify the resultant product in a manner similar to that described to obtain 9α-fluoro-16β-methyl-11β,17α-diol-3,11,20-trione 17,21-methylorthobutyrate.

B. In a manner similar to that described hereinabove, treat 9α-fluoro-16β-methyl-4-pregnene-17α,21-diol-3,11,20-trione in dimethylsulfoxide with p-toluenesulfonic acid and trimethylortho-n-butyrate to obtain 9α-fluoro-16β-methyl-4-pregnene-17α,21-diol-3,11,20-trione 17,21-methylortho-n-butyrate.

PREPARATION 11

6α,9α-difluoro-16β-methyl-1,4-pregnadiene-11β,17α,21-triol-3,20-dione 17,21-ethylorthoacetate and the 1,2-dihydro analog thereof A. In a manner similar to that described in Preparation 5A, treat 6α,9α-difluoro-16β-methyl-1,4-pregnadiene-11β,17α,21-triol-3,20-dione in dimethylsulfoxide with p-toluenesulfonic acid and triethylorthoacetate. Isolate and purify the resultant product in a manner similar to that described to obtain 6α,9α-difluoro-16β-methyl-1,4-pregnadiene-11β,17α,21-triol-3,20-dione 17,21-ethylorthoacetate.

B. In a manner similar to that described hereinabove, treat 6α,9α-difluoro-16β-methyl-4-pregnene-11β,17α,21-triol-3,20-dione in dimethylsulfoxide with p-toluenesulfonic acid and triethylorthoacetate to obtain 6α,9α-difluoro-16β-methyl-4-pregnene-11β,17α,21-triol-3,20-dione 17,21-ethylorthoacetate.

PREPARATION 12

1,4-pregnadiene-11β,17α,21-triol-3,20-dione 17,21-ethylorthopropionate

To a solution of prednisolone (5 gm.) in dimethylsulfoxide (25 ml.) add p-toluenesulfonic acid (375 mg.) and triethylorthopropionate (9.0 ml.). Stir at room temperature for 3 hours, then pour into water (200 ml.) and add saturated sodium bicarbonate solution (200 ml.). Extract the aqueous mixture with ethyl acetate (three 200 ml. portions), wash the combined organic extracts with water (three 150 ml. portions), dry over anhydrous magnesium sulfate and evaporate. Triturate the resultant residue with hexane to give 1,4-pregnadiene-11β,17α,21-triol-3,20-dione (5.5 gm.).

EXAMPLE 1

9α,11β,21-trichloro-16α-methyl-1,4-pregnadiene-17α-ol-3,20-dione 17-benzoate and the 1,2-dihydro analog thereof A. Dissolve the 9α,11β-dichloro-16α-methyl-1,4-pregnadiene-17α,21-diol-3,20-dione 17,21-methylorthobenzoate obtained as described in Preparation 1A in 120 ml. of methylene chloride, add 2.4 ml. of trimethylsilyl chloride and heat the reaction mixture at reflux temperature under an atmosphere of nitrogen for 22 hours, then evaporate in vacuo at room temperature and chromatograph the resultant residue on 200 gms. of silica gel eluting with a solvent mixture comprising ethyl acetate/chloroform (1:50). Combine the like fractions as determined by thin layer chromatography and evaporate to a residue comprising 9α,11β,21-trichloro-16α-methyl-1,4-pregnadiene-17α-ol-3,20-dione 17-benzoate (yield=0.97 gm., 38% theory). Further purify by crystallization from acetone to obtain 9α,11β,21-trichloro-16α-methyl-1,4-pregnadiene-17α-ol-3,20-dione 17-benzoate, m.p. 232–234° C; $[α]_D^{26}$ + 58.4° (dimethylformamide); $λ_{max}^{methanol}$, 233 nm (30,250); nmr (dmso-$d_6$) δ0.89 ($C_{16}$-$CH_3$; dJ 8Hz), 1.13 ($C_{13}$-$CH_3$; s), 1.73 ($C_{10}$-$CH_3$; s), 4.56 ($C_{21}$-$CH_2$; s), 5.08 (11α-H; mult), 7.80 (phenyl).

B. In a manner similar to that described hereinabove, treat the product obtained in Preparation 1B with trimethylsilyl chloride in methylene chloride under an atmosphere of nitrogen. Isolate and purify the resultant product in a manner similar to that described to obtain 9α,11β,21-trichloro-16α-methyl-4-pregnene-17α-ol-3,20-dione 17-benzoate.

EXAMPLE 2

21-bromo-1,4-pregnadiene-11β,17α-diol-3,20-dione 17-propionate and the 1,2-dihydro analog thereof

A.

21-bromo-1,4-pregnadiene-11β,17α-diol-3,20-dione 11-trimethylsilyl ether 17-propionate and the 1,2-dihydro analog thereof 1. To a solution of 0.2 gms. of 1,4-pregnadiene-11β,17α,21-triol-3,20-dione 17,21-n-butylorthopropionate in 20 ml. of methylene chloride add 0.28 ml. of trimethylsilyl bromide (5 molar equivalents) and heat the reaction mixture at reflux temperature for 21 hours. Evaporate the reaction mixture in vacuo and chromatograph the resultant residue on 20 gms. of silica gel eluting with solvent mixture comprising ethyl acetate/chloroform (1:2). Combine the like eluates as determined by thin layer chromatography and evaporate to a residue comprising 21-bromo-1,4-pregnadiene-11β,17α-diol-3,20-dione 11-trimethylsilyl ether 17-propionate (yield = 31 mg., 15% theory).

2. In a manner similar to that described in Example 2A(1) treat 4-pregnene-11β,17α,21-triol-3,20-dione 17,21-butylorthopropionate with trimethylsilyl bromide in methylene chloride to obtain 21-bromo-4-pregnene-11β,17α-diol-3,20-dione 11-trimethylsilyl ether 17-propionate.

B.

21-bromo-1,4-pregnadiene-11β,17α-diol-3,20-dione 17-propionate and the 1,2-dihydro analog thereof 1. Dissolve the 31 mg. of 21-bromo-1,4-pregnadiene-11β,17α-diol-3,20-dione 11-trimethylsilyl ether 17-propionate obtained as described in Example 2A(1) in 3 ml. of methanol and add 0.45 ml. of 6 N hydrochloric acid. Allow the solution to stand at room temperature for 24 hours, then add water, filter off the resultant precipitate, wash the precipitate with water, dry and crystallize from methanol/chloroform/hexane to obtain 21-bromo-1,4-pregnadiene-11β,17α-diol-3,20-dione 17-propionate.

2. In a manner similar to that described in Example 2B(1) treat 21-bromo-4-pregnene-11β,17α-diol-3,20-dione 11-trimethylsilyl ether 17-propionate with hydrochloric acid in methanol and isolate the resultant product to obtain 21-bromo-4-pregnene-11β,17α-diol-3,20-dione 17-propionate.

EXAMPLE 3

21-chloro-1,4-pregnadiene-11β,17α-diol-3,20-dione 17-propionate and the 1,2-dihydro analog thereof A. To 1 gm. of 1,4-pregnadiene-11β,17α,21-triol-3,20-dione 17,21-n-butylorthopropionate in 50 ml. of methylene chloride add 1.36 ml. of trimethylsilyl chloride and heat the reaction mixture at reflux temperature under an atmosphere of nitrogen for 2.5 hours. Evaporate the reaction mixture in vacuo and chromatography the resultant residue on 120 gms. of silica gel eluting with chloroform/ethyl acetate (2:1). Combine the like eluates as determined by thin layer chromatography and evaporate the combined eluates to a residue comprising 21-chloro-1,4-pregnadiene-11β,17α-diol-3,20-dione 17-propionate (yield=0.49 g; 54% theory). Purify by crystallization from acetone/methylene chloride, m.p. 221–225° C; $[α]_D^{26}$ + 69.9 (dimethylformamide), mass spectrum m/e 436,434 [M]$^+$; nmr (dmso-$d_6$) δ0.88 ($C_{13}$-$CH_3$); 1.40 ($C_{10}$-$CH_3$); 4.40 ($C_{21}$–$CH_2$; s).

B. In a manner similar to that described in Example 3A treat the 4-pregnene 17,21-n-butylorthopropionate obtained in Preparation 2B with trimethylsilyl chloride in methylene chloride under an atmosphere of nitrogen to obtain 21-chloro-4-pregnene-11β,17α-diol-3,20-dione 17-propionate.

Alternatively, the 1,4-pregnadiene of this example is prepared according to following procedure C.

C. To 0.2 gm. of 1,4-pregnadiene-11β,17α,21-triol-3,20-dione 17,21-n-butylorthopropionate in 20 ml. of methylene chloride add 0.625 gm. (5 equivalents) of triphenylsilyl chloride, then heat the reaction mixture at reflux temperature for 22 hours. Evaporate the reaction mixture in vacuo and chromatograph the resultant residue on 20 gm. of silica gel eluting with chloroform/ethyl acetate (3:1). Combine the like eluates as determined by thin layer chromatography and evaporate the combined eluates to a residue comprising 21-chloro- 1,4-pregnadiene-11β,17α-diol-3,20-dione 17-propionate (yield 77.5 mg., 42% theory) having nmr and mass spectrum identical to that of the compound prepared as described in Example 3A.

Treat 4-pregnene-11β,17α,21-triol-3,20-dione 17,21-n-butylorthopropionate in methylene chloride with triphenylsilyl chloride in a manner similar to that described hereinabove. Isolate the resultant product in a similar manner to that described, to obtain 21-chloro-4-pregnene-11β,17α-diol-3,20-dione 17-propionate.

Alternatively, the compounds of this example are prepared according to following procedures D and E.

D. To 1,4-pregnadiene-11β,17α,21-triol-3,20-dione 17,21-ethylorthopropionate (5.5 gm.) in methylene chloride (250 ml.) add trimethylsilyl chloride (9 ml.) and heat the reaction mixture for 19 hours. Evaporate the reaction mixture and chromatograph the resultant residue on silica gel (550 gm.) eluting with chloroform:ethyl acetate (2:1). Combine the like eluates as determined by thin layer chromtrography and evaporate the combined eluates to a residue comprising 21-chloro-1,4-pregnadiene-11β,17α,21-triol-3,20-dione 17,21-propionate; yield 3.9 gm. (65% theory).

E. preparation of 21-chloro-1,4-pregnadiene-11β,17α-diol-3,20-dione 17-propionate without chromatographic purification To a solution of 1,4-pregnadiene-11β,17α,21-triol-3,20-dione 17,21-ethylorthopropionate (1 gm.) in methylene chloride (50 ml.) add trimethylsilyl chloride (1.8 ml.) and heat at reflux temperature for 17 hours. Evaporate the reaction mixture in vacuo and crystallize the resultant residue from acetone. Separate the resultant precipitate by filtration and dry the resultant precipitate to give 21-chloro-1,4-pregnadiene-11β,17α-diol-3,20-dione 17-propionate; yield 0.5 gm., (50% theory).

EXAMPLE 4

9α,11β,21-trichloro-16α-methyl-1,4-pregnadiene-17α-ol-3,20-dione 17-propionate and the 1,2-dihydro analog thereof A. Dissolve 1 gm. of 9α,11β-dichloro-16α-methyl-1,4-pregnadiene-17α,21-diol-3,20-dione 17,21-n-butylorthopropionate in 50 ml. of methylene chloride, add 1.23 ml. of trimethylsilyl chloride and heat the reaction mixture at reflux temperature for 4 hours, then evaporate in vacuo at room temperature and chromatograph the resultant residue on 85 gm. of silica gel eluting with chloroform:ethyl acetate (8:1). Combine the like fractions as determined by thin layer chromatography and evaporate to a residue comprising 9α,11β,21-trichloro-16α-methyl-1,4-pregnadiene-17α-ol-3,20-dione 17-propionate (0.3 gm., 41% theory). Further purify by crystallization from methylene chloride/ethyl acetate, m.p. 242°–246° C; $[\alpha]_D^{26}$ + 124.2 (dimethylformamide); nmr (dmso-d$_6$); δ 1.03 ($C_{13}$-$CH_3$); 1.69 ($C_{10}$-$CH_3$); 4.25 ($C_{21}$-$CH_2$; s).

B. In a manner similar to that described in Example 4A treat 9α,11β-dichloro-16α-methyl-4-pregnene-17α,21-diol-3,20-dione 17,21-n-butylorthopropionate with trimethylsilyl chloride in methylene chloride to obtain 9α,11β,21-trichloro-16α-methyl-4-pregnene-17α-ol-3,20-dione 17-propionate.

EXAMPLE 5

9α,11β,21-trichloro-16α-methyl-1,4-pregnadiene-17α-ol-3,20-dione 17-valerate and the 1,2-dihydro analog thereof A. Dissolve 0.7 gm. of 9α,11β-dichloro-16α-methyl-1,4-pregnadiene-17α,21-diol-3,20-dione 17,21-n-butylorthovalerate in 35 ml. of methylene chloride, add 0.88 ml. of trimethylsilyl chloride and heat the reaction mixture for 3 hours. Evaporate at room temperature in vacuo and chromatograph the resultant residue on 70 gm. of silica gel eluting with chloroform:ethyl acetate (5:1). Combine the like fractions as determined by thin layer chromatography and evaporate to a residue comprising 9α,11β,21-trichloro-16α-methyl-1,4-pregnadiene-17α-ol-3,20-dione 17-valerate (0.45 gm., 65% theory). Purify further by recrystallization from methylene chloride in acetone, m.p. 211°–213° C; $[\alpha]_D^{26}$ + 104.4 (dimethylformamide); nmr (dmso-d$_6$); δ 1.10 ($C_{13}$-$CH_3$); 1.75 ($C_{10}$-$CH_3$); 4.49 ($C_{21}$-$CH_2$; s).

B. In a manner similar to that described in Example 5A treat 9α,11β-dichloro-16α-methyl-4-pregnene-17α,21-diol-3,20-dione 17,21-n-butylorthovalerate with trimethylsilyl chloride in methylene chloride. Isolate and purify the resultant product in the described manner to obtain 9α,11β-trichloro-16α-methyl-4-pregnene-17α-ol-3,20-dione 17-valerate.

EXAMPLE 6

9α-fluoro-21-chloro-16β-methyl-1,4-pregnadiene-11β,17α-diol-3,20-dione 17-propionate and the 1,2-dihydro analog thereof A. To 3.4 gm. of 9α-fluoro-16β-methyl-1,4-pregnadiene-11β,17α,21-triol-3,20-dione 17,21-n-butylorthopropionate in 250 ml. of methylene chloride, add 4.36 ml. of trimethylsilyl chloride and heat the reaction mixture at reflux temperature for 24 hours. Evaporate the reaction mixture in vacuo and chromatograph the resultant residue on 220 gm. of silica gel eluting with chloroform:ethyl acetate (3:1). Combine the like fractions as determined by thin layer chromatography and evaporate the combined fractions in vacuo to a residue comprising 9α-fluoro-21-chloro-16β-methyl-1,4-pregnadiene-11β,17α-diol-3,20-dione 17-propionate (yield 0.18 gm., 6% theory).

B. In a manner similar to that described in Example 6A treat 9α-fluoro-16β-methyl-4-pregnene-11β,17α,21-triol-3,20-dione 17,21-n-butylorthopropionate with trimethylsilyl chloride in chloroform and isolate the resultant product to obtain 9α-fluoro-21-chloro-16β-methyl-4-pregnene-11β,17α-diol-3,20-dione 17-propionate.

EXAMPLE 7

16α-methyl-21-chloro-1,4-pregnadiene-11β,17α-diol-3,20-dione 17-propionate and the 1,2-dihydro analog thereof A. Dissolve the 16α-methyl-1,4-pregnadiene-11β,17α,21-triol-3,20-dione 17,21-n-butylorthopropionate obtained in Preparation 2A in 87 ml. of methylene chloride, add 1.15 ml. (5 equivalents) of trimethylsilyl chloride and heat the reaction mixture at reflux temperature for 24 hours. Evaporate the reaction mixture in vacuo and chromatograph the resultant residue on 80 gm. of silica gel eluting with chloroform:ethyl acetate (2:1). Combine the like fractions as determined by thin layer chromatography and evaporate the combined fractions in vacuo to a residue comprising 16α-methyl-21-chloro-1,4-pregnadiene-11β,17α-diol-3,20-dione 17-propionate (yield 0.4 gm., 44% theory); m.p. 255°–258° C, $[\alpha]_{D\ 26} + 81.1$ (dimethylformamide) nmr (dmso-d$_6$); δ 0.94 (C$_{13}$–CH$_3$); 1.39 (C$_{10}$–CH$_3$); 4.30 (C$_{21}$–CH$_2$; s).

B. In a manner similar to that described in Example 7A treat 16α-methyl-4-pregnene-11β,17α,21-triol-3,20-dione 17,21-n-butyl-orthopropionate in methylene chloride with trimethylsilyl chloride and isolate and purify the resultant product in the described manner to obtain 16α-methyl-21-chloro-4-pregnene-11β,17α-diol-3,20-dione 17-propionate.

EXAMPLE 8

9α-fluoro-21-chloro-16α-methyl-1,4-pregnadiene-11β,17α-diol-3,20-dione 17-benzoate and the 1,2-dihydro analog thereof A. Dissolve the 9α-fluoro-16α-methyl-1,4-pregnadiene-11β,17α,21-triol-3,20-dione 17,21-methylorthobenzoate prepared in Preparation 8A in 60 ml. of methylene chloride, add 1.2 ml. of trimethylsilyl chloride, heat the reaction mixture at reflux temperature for 2 hours, then evaporate at room temperature in vacuo. Chromatograph the resultant residue on 100 gm. of silica gel eluting with chloroform:methylene chloride:ethyl acetate (25:25:1). Combine the like fractions as determined by thin layer chromatography and evaporate the combined fractions in vacuo to a residue comprising 9α-fluoro-21-chloro-16α-methyl-1,4-pregnadiene-11β,17α-diol-3,20-dione 17-benzoate; m.p. 255°–257° C; $[\alpha]_D^{26} + 5.7$ (dimethylformamide); nmr (dmso-d$_6$); δ 1.04 (C$_{13}$–CH$_3$); 1.52 (C$_{10}$-CH$_3$); 4.50 (C$_{21}$-CH$_2$; s); 7.80 (phenyl), (yield=0.45 g.; 34% theory).

B. Treat 9α-fluoro-16α-methyl-4-pregnene-11β,17α,21-triol-3,20-dione 17,21-methylorthobenzoate in methylene chloride with trimethysilyl chloride in the manner of Example 8A. Isolate the resultant product in a manner similar to that described to obtain 9α-fluoro-21-chloro-16α-methyl-4-pregnene-11β,17α-diol-3,20-dione 17-benzoate.

EXAMPLE 9

9α-fluoro-21-bromo-16α-methyl-1,4-pregnadiene-11β,17α-diol-3,20-dione 17-propionate and the 1,2-dihydro analog thereof A. To a solution of 1 gm. of 9α-fluoro-16α-methyl-1,4-pregnadiene-11β,17α,21-triol-3,20-dione 17,21-n-butylorthopropionate in 50 ml. of methylene chloride add 1.309 ml. (5 molar equivalents) of trimethylsilyl bromide. Heat the reaction mixture at reflux temperature for 2 hours under anhydrous conditions. Evaporate the reaction mixture in vacuo and chromatograph the resultant residue on 100 gm. of silica gel eluting with chloroform:ethyl acetate (4:1). Combine the like eluates as determined by thin layer chromatography and evaporate the combined eluates to a residue comprising 9α-fluoro-21-bromo-16α-methyl-1,4-pregnadiene-11β,17α-diol-3,20-dione 17-propionate; yield=0.65 g.; 65% theory; m.p.=242°–245° C; $[\alpha]_D^{26}$ +93.4° (dimethylformamide).

B. In a manner similar to that described in Example 9A treat 9α-fluoro-16α-methyl-4-pregnene-11β,17α,21-triol-3,20-dione 17,21-n-butylorthopropionate in methylene chloride with trimethylsilyl bromide to obtain 9α-fluoro-21-bromo-16α-methyl-4-pregnene-11β,17α-diol-3,20-dione 17-propionate.

EXAMPLE 10

21-chloro-1,4,6-pregnatriene-11β,17α-diol-3,20-dione 17-propionate and the 1,2-dihydro analog thereof A. Dissolve the 1,4,6-pregnatriene-11β,17α,21-triol-3,20-dione 17,21-n-butylorthopropionate prepared in Preparation 9A in 10 ml. of methylene chloride. Add 0.108 ml. of trimethylsilyl chloride and heat the reaction mixture at reflux temperature for 21 hours. Evaporate the solvent in vacuo and chromatograph the resultant residue on a thin layer chromatographic plate (silica gel) developing with chloroform:ethyl acetate (1:1). Scrape off the band of product and elute with ethyl acetate. Evaporate the ethyl acetate eluates to a residue comprising 21-chloro-1,4,6-pregnatriene-11β,17α-diol-3,20-dione 17-propionate (yield 11 mg., 15% theory); mass spectrum m/e 434,432 [M]$^+$.

B. In a manner similar to that described in Example 10A treat 4,6-pregnadiene-11β,17α,21-triol-3,20-dione 17,21-n-butyl-orthopropionate in methylene chloride with trimethylsilyl chloride to obtain 21-chloro-4,6-pregnadiene-11β,17α-diol-3,20-dione 17-propionate.

EXAMPLE 11

9α-fluoro-21-chloro-16α-methyl-1,4-pregnadiene-11β,17α-diol-3,20-dione 17-propionate and the 1,2-dihydro analog thereof A. Procedure Utilizing Trityl Chloride To a solution of 1.3 gm. of 9α-fluoro-16α-methyl-1,4-pregnadiene-11β,17α,21-triol-3,20-dione 17,21-n-butylorthopropionate in 65 ml. of methylene chloride add 3.59 gm. (5 molar equivalents) of trityl chloride. Heat the reaction mixture at reflux temperature for 22 hours under anhydrous conditions. Evaporate the reaction mixture to a residue, add 50% aqueous acetic acid to the residue and stir for 10 minutes, extract the acetic acid mixture with methylene chloride and evaporate the combined methylene chloride extracts in vacuo to a residue. Chromatograph the residue on a column of silica gel eluting with chloroform:ethyl acetate (3:1). Combine the like eluates as determined by thin layer chromatography and evaporate the combined eluates in vacuo to a residue comprising 9α-fluoro-21-chloro-16α-methyl-1,4-pregnadiene-11β,17α-diol-3,20-dione 17-propionate (yield 0.26 gm., 22% theory).

B. Procedure Utilizing Trimethylsilyl Chloride

To a solution of 100 mg. of 9α-fluoro-16α-methyl-1,4-pregnadiene-11β,17α,21-triol-3,20-dione 17,21-n-butylorthopropionate in 5 ml. of methylene chloride add 260 mg. (5 molar equivalents) of trimethylsilyl chloride. Heat the reaction mixture at reflux temperature for 2.5 hours under anhydrous conditions. (Thin layer chromatogrpahic analysis indicates very little starting ortho ester present). Evaporate the reaction mixture in vacuo and apply the resultant residue to thin layer chromatographic plates developing with chloroform:ethyl acetate (3:1). Elute the least polar band and evaporate the eluates to a residue comprising 9α-fluoro-21-chloro-16α-methyl-1,4-pregnadiene-11β,17α,21-triol-3,20-dione 17-propionate (yield 51 mg., 55% theory); nmr (dmso-d$_6$); δ 0.83 (C$_{16}$-CH$_3$; dJ7Hz); 0.94 (C$_{13}$-CH$_3$); 1.49 (C$_{10}$-CH$_3$); 4.16 (11α-OH; mult.); 4.33 (C$_{21}$-CH$_2$; s); mass spectrum m/e 468,466 [M]$^+$ (weak).

Carry out the procedures described in Example 11B, starting with 9α-fluoro-16α-methyl-4-pregnene-11β,17α,21-triol-3,20-dione 17,21-n-butylorthopropionate to obtain 9α-fluoro-21-chloro-16α-methyl-4-pregnene-11β,17α-diol-3,20-dione 17-propionate.

EXAMPLE 12

9α-fluoro-21-chloro-16β-methyl-1,4-pregnadiene-17α-ol-3,11,20-trione 17-(n-butyrate) and the 1,2-dihydro analog thereof A. In a manner similar to that described in Example 6A treat 9α-fluoro-16β-methyl-17α,21-diol-3,11,20-trione 17,21-methylortho-n-butyrate in methylene chloride with trimethylsilyl chloride. Isolate and purify the resultant product in a manner similar to that described to obtain 9α-fluoro-21-chloro-16β-methyl-1,4-pregnadiene-17α-ol-3,11,20-trione 17-n-butyrate.

B. Carry out the procedure of Example 12A utilizing as starting compound 9α-fluoro-16β-methyl-4-pregnene-17α,21-diol-3,11,20-trione 17,21-methylortho-n-butyrate to obtain 9α-fluoro-21-chloro-16β-methyl-4-pregnene-17α-ol-3,11,20-trione 17-n-butyrate.

EXAMPLE 13

6α,9α-difluoro-21-chloro-16β-methyl-1,4-pregnadiene-11β,17α-diol-3,20-dione 17-acetate and the 1,2-dihydro analog thereof A. In a manner similar to that described in Example 6A treat 6α,9α-difluoro-16β-methyl-1,4-pregnadiene-11β,17α,21-triol-3,20-dione 17,21-ethylorthoacetate in methylene chloride with trimethylsilyl chloride. Isolate and purify the resultant product in a manner similar to that described to obtain 6α,9α-difluoro-21-chloro-16β-methyl-1,4-pregnadiene-11β,17α-diol-3,20-dione 17-acetate.

B. Treat 6α,9α-difluoro-16β-methyl-4-pregnene-11β,17α,21-triol-3,20-dione 17,21-ethylorthoacetate in methylene chloride with trimethylsilyl chloride in the manner of Example 6B to obtain 6α,9α-difluoro-21-chloro-16β-methyl-1,4-pregnadiene-11β,17α-diol-3,20-dione 17-acetate.

I claim:

1. The process for the preparation of a 21-halogeno-17α-acyloxy-20-ketopregnene, said halogeno being chloro or bromo, which comprises the reaction of a 17,21-dihydroxy-20-ketopregnene 17,21-orthoester with a halide reagent selected from the group consisting of triphenylsilyl halide, tri-(alkyl substituted phenyl)-silyl halide, and tri-lower alkylsilyl halide, said halide being chloride or bromide, in an organic solvent.

2. A process in accordance with claim 1 wherein the organic solvent is a halogenated hydrocarbon, and said process is carried out at the relux temperature of said solvent.

3. The process of claim 1 wherein said halide reagent is trimethylsilyl halide.

4. The process of claim 1 wherein said 17,21-dihydroxy-20-ketopregnene 17,21-orthoester is a member selected from the group consisting of a compound defined by formula I:

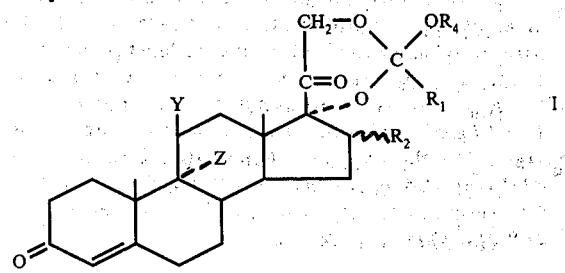

I wherein Y is hydrogen, oxo, hydroxy, lower alkanoyloxy, chlorine or fluorine;
Z is hydrogen, fluorine, chlorine or bromine when Y is oxo, hydroxy or lower alkanoyloxy; Z is chlorine or bromine when Y is chlorine or fluorine; and Z is hydrogen when Y is hydrogen
$R_1$ is alkyl of 1 to 8 carbon atoms, or phenyl;
$R_2$ is hydrogen, α-methyl, β-methyl, α-acyloxy of the formula

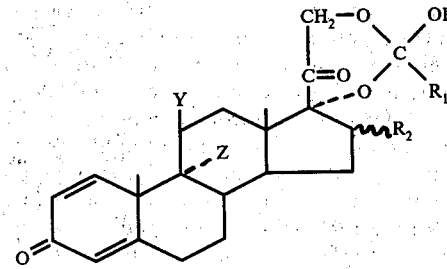

wherein $R_3$ is a lower alkyl having 1 to 8 carbon atoms;
$R_4$ is alkyl having 1 to 4 carbon atoms;
and the 1-dehydro-, 6-dehydro- and 1,6-bis-dehydro analogs of the compounds of formula I.

5. The process of claim 4 wherein the 17α,21-dihydroxy-20-ketopregnene 17,21-orthoester is a compound of the formula:

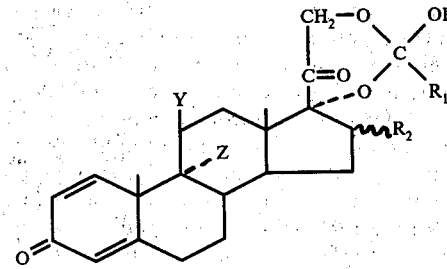

6. A process for preparing a 21-chloro-17-acyloxy-20-ketopregnene from a 17,21-dihydroxy-20-ketopregnene 17,21-orthoester which comprises reacting a 17,21-dihydroxy-20-ketopregnene 17,21-orthoester with trimethylsilyl chloride in a halogenated hydrocarbon solvent at the reflux temperature of said solvent.

7. The process of claim 6 wherein the 17,21-dihydroxy-20-ketopregnene 17,21-orthoester has the formula:

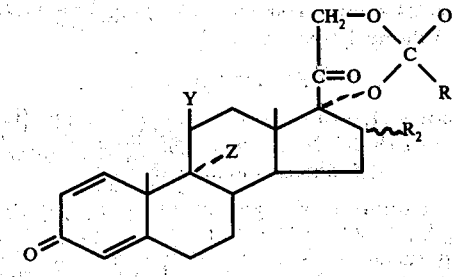

wherein
Y is hydroxy or chlorine;
Z is hydrogen, fluorine, chlorine, or bromine when Y is hydroxy, and Z is chlorine when y is chlorine;
$R_1$ is alkyl of 1 to 8 carbon atoms, or phenyl;
$R_2$ is hydrogen, α-methyl, β-methyl, α-acyloxy of the formula

wherein $R_3$ is a lower alkyl having 1 to 8 carbon atoms; and
$R_4$ is alkyl of 1 to 4 carbon atoms.

* * * * *

UNITED STATES PATENT OFFICE
CERTIFICATE OF CORRECTION

Patent No. 3,992,422    Dated November 16, 1976

Inventor(s) Michael J. Green

It is certified that error appears in the above-identified patent and that said Letters Patent are hereby corrected as shown below:

Column 2, line 44, "$-R_3-\overset{O}{\underset{}{C}}-O-$" should read ---$R_3-\overset{O}{\underset{}{C}}-O-$---.
Column 8, line 23, "dimetyl" should read ---dimethyl---.
Column 11, line 20, "chromtrography" should read ---chromatography---. Column 12, line 27, "-9α,11β-trichloro-" should read ---9α,11β,21-trichloro---. Column 13, line 5, "$[\alpha]_D$" should read ---$[\alpha]_D^{26}$---. Column 14, line 57, "chromatogrpahic" should read ---chromatographic---. Column 16, line 57, "when y is" should read ---when Y is---.

Signed and Sealed this

Eighth Day of February 1977

[SEAL]

Attest:

RUTH C. MASON
Attesting Officer

C. MARSHALL DANN
Commissioner of Patents and Trademarks